US006635423B2

(12) United States Patent
Dooley et al.

(10) Patent No.: US 6,635,423 B2
(45) Date of Patent: Oct. 21, 2003

(54) INFORMATIVE NUCLEIC ACID ARRAYS AND METHODS FOR MAKING SAME

(75) Inventors: Thomas P. Dooley, Vestavia Hills, AL (US); Ernest V. Curto, Huntsville, AL (US); Richard L. Davis, Jr., Huntsville, AL (US)

(73) Assignee: Integriderm, Inc., Birmingham, AL (US)

( * ) Notice: Subject to any disclaimer, the term of this patent is extended or adjusted under 35 U.S.C. 154(b) by 0 days.

(21) Appl. No.: 09/759,377

(22) Filed: Jan. 16, 2001

(65) Prior Publication Data
US 2001/0046671 A1 Nov. 29, 2001

Related U.S. Application Data

(60) Provisional application No. 60/176,022, filed on Jan. 14, 2000, and provisional application No. 60/197,991, filed on Apr. 18, 2000.

(51) Int. Cl.[7] .......................... C12Q 1/68; G01N 33/53; G01N 33/58; G01N 33/60; G01N 33/48; C07H 21/04; G01F 19/00
(52) U.S. Cl. ......................... 435/6; 435/968; 435/97.3; 436/63; 536/24.3; 702/19
(58) Field of Search ........................... 435/6, 968, 973; 536/24.3; 436/63; 702/19

(56) References Cited

U.S. PATENT DOCUMENTS

| 5,569,588 A | * 10/1996 | Ashby et al. ................. 435/6 |
| 5,707,807 A | 1/1998 | Kato |
| 5,807,522 A | 9/1998 | Brown et al. |
| 5,846,708 A | 12/1998 | Hollis et al. |
| 5,922,617 A | 7/1999 | Wang et al. |
| 5,965,352 A | 10/1999 | Stoughton et al. |
| 5,968,784 A | 10/1999 | Spinella et al. |
| 5,994,076 A | 11/1999 | Chenchik et al. |
| 6,004,755 A | 12/1999 | Wang |

FOREIGN PATENT DOCUMENTS

| WO | WO98/30722 | 7/1998 |
| WO | WO98/53103 | 11/1998 |
| WO | WO99/54724 | 10/1999 |
| WO | WO99/55913 | 11/1999 |
| WO | WO99/58720 | 11/1999 |
| WO | WO99/60450 | 11/1999 |

OTHER PUBLICATIONS

Chen, Yidong, et al., "Ratio–Based Decisions and the Quantitative Analysis of cDNA Microarray Images" Journal of Biomedical Optics, International Society for Optical Engineering (SPIE), US, vol. 2, No. 4, Oct. 1997, pp. 364–374, 1083–3668.

Marton, M J et al., "Drug Target Validation and Identification of Secondary Drug Target Effects Using DNA Microarrays" Nature Medicine, Nature Publishing Co., US, vol. 4, No. 11, Nov. 1998, pp. 1293–1301, 1078–8956.

* cited by examiner

Primary Examiner—Kenneth R. Horlick
Assistant Examiner—Teresa Strzelecka
(74) Attorney, Agent, or Firm—Morrison & Foerster LLP

(57) ABSTRACT

The present invention is directed to methods for making and using informative nucleic acid arrays (e.g., DNA including cDNA, RNA, PNA) for research and other applications in various disciplines or areas of interest. Examples of such disciplines include, without limitation, dermatology, pharmacology, toxicology, oncology, gynecology, urology, gastroenterology, as well as studies of sentinel gene discovery, signature gene discovery, mechanism of action, drug screening, drug metabolism, etc. The informative nucleic acid arrays of the present invention may contain only the gene sequences that are of interest in a particular area of interest or application, and may exclude other gene sequences.

30 Claims, 3 Drawing Sheets

INFORMATIVE NUCLEIC ACID ARRAYS AND METHODS FOR MAKING SAME

CROSS-REFERENCE TO RELATED APPLICATIONS

The present invention claims the benefit of U.S. Provisional Patent Application No. 60/176,022, filed Jan. 14, 2000, and U.S. Provisional Patent Application No. 60/197,991, filed Apr. 18, 2000.

BACKGROUND OF THE INVENTION

1. Field of the Invention

The present invention relates generally to nucleic acid arrays and to methods for designing and using nucleic acid arrays. In particular, the present invention relates to informative nucleic acid arrays and methods for making the same, with an emphasis on the selection criteria for the individual gene sequences to be included in informative nucleic acid arrays.

2. Description of the Related Art

In general, most of the cells of an organism contain the same gene sequences. In eucaryotic organisms (i.e., those having a nucleus) the number of individual genes typically is in the range of tens of thousands of genes. All of these genes, however, are not used or expressed by all cells all of the time. Some genes are activated, or expressed, only at a specific time, at a specific level, at a specific developmental stage, and/or in a specific cellular, physiologic, and/or tissue context. Determining when a gene is expressed, and what causes the gene to be expressed, may be key in better understanding the effects of various agents on cellular responses (e.g., potential pharmaceuticals, toxins, chemicals, temperature, pressure, or electromagnetic radiation, etc.). In addition, determining when a gene is expressed may yield a better understanding of the effects of various normal or variant genes on disease pathogenesis (e.g., induced or hereditary disorders, etc.).

To this end, a variety of molecular biology methods for classifying, indexing, and/or quantifying nucleic acid with regard to gene expression have been proposed. For example, U.S. Pat. No. 5,707,807 relates to a method for classifying cDNA that has been reverse-transcribed from tissue- or cell-derived RNA. The method is also applicable to the search and isolation of genes of physiologically active substances that are potential pharmaceuticals or causative genes of hereditary diseases, as well as the isolation of those genes that are useful for improving agricultural products.

Another example of gene expression analysis is in U.S. Pat. No. 5,968,784. This patent relates to a method for tagging and identifying all of the expressed genes in a given cell population. By comparing gene expression profiles among cells, the method may be used to identify individual genes whose expression is associated with a pathological phenotype. U.S. Pat. No. 5,968,784 also relates to methods for identifying gene expression patterns in an mRNA population to identify differential gene expression patterns among two or more cells or tissues.

Another useful contemporary methodology for analyzing simultaneously a plurality of genes for gene expression levels utilizes nucleic acid arrays (or microarrays or macroarrays, hereinafter collectively referred to as arrays). DNA arrays typically consist of hundreds to thousands of immobilized DNA sequences present on a surface of an object the size of a business card or smaller. The nucleic acids for the selected individual gene sequences are immobilized on the surfaces of nylon filters, glass, plastic, or gene chips, etc. Robotic technologies may be employed in the production of arrays. Labeled probe samples are prepared from RNA from biological samples. The probes are hybridized to the immobilized nucleic acids on the arrays, and a detector instrument collects the intensities of hybridization of the bound labeled probe sample to the individual gene sequences. Then, computer software typically analyses the results. For example, U.S. Pat. No. 5,807,522 relates to a method and apparatus for forming arrays of biological samples on a support in an automated fashion. U.S. Pat. No. 5,922,617 relates to a product having arrays of samples in tracks, wherein light emitting labels are excited and emitted light is detected. For example, the arrays may be located in circular tracks on a compact disc-like support. In addition, U.S. Pat. No. 5,922,617 relates to a reader for determining the occurrence of events on the array.

With regard to the methodologies for selecting individual gene sequences for inclusion on arrays, currently available gene expression arrays typically consist of one of two types of gene selection methods. In one case, gene sequences that are merely available to the designer are immobilized on an array, regardless of any biological significance of the selected gene sequences or as the result of experimentation. In the other case, gene sequences that are expressed in one cell type or tissue type are chosen for inclusion on the array. Both of these conventional gene selection methodologies produce general utility arrays that have limited "informative" capabilities. This disadvantage is especially pronounced if the general arrays contain a relatively small number of immobilized gene sequences, thus reducing the likelihood that one will discover differentially expressed gene sequences during experimentation. Although arrays are becoming more widely known and used, very little attention has been paid to the creation or use of informative nucleic acid arrays.

SUMMARY OF THE INVENTION

Thus, a need has arisen for informative nucleic acid arrays, and for methods for selecting the individual gene sequences for inclusion on the informative arrays, and for making the same.

As embodied and broadly described herein, the present invention is directed to methods for making and using informative nucleic acid arrays (e.g., DNA including cDNA, RNA, PNA) for research and other applications in various disciplines or areas of interest. Examples of such disciplines include, without limitation, dermatology, pharmacology, toxicology, oncology, gynecology, urology, gastroenterology, as well as studies of sentinel gene discovery, signature gene discovery, mechanism of action, drug screening, drug metabolism, etc. The informative nucleic acid arrays of the present invention may contain only the gene sequences that are of interest in a particular area of interest or application, and may exclude other gene sequences.

According to one embodiment of the present invention, a method for identifying genes that are differentially expressed between dissimilar biological samples for use in an informative array is disclosed. The method includes the steps of (1) providing a first set of heterogeneous nucleic acid probes derived from a first biological sample; (2) providing a second set of heterogeneous nucleic acid probes derived from a second biological sample wherein the first and second biological samples are different and have a common biological process; (3) hybridizing a nucleic acid array comprising a plurality of sequences derived from genes of the biological process with the first set of probes and determining a first level of expression for sequences of the array; (4) hybridizing the array with the second set of probes and determining a second level of expression for sequences of the array; and (5) identifying a plurality of genes that are differentially expressed in the biological process by comparing the first level of expression with the second level of expression for hybridized sequences. The biological process may include the processes of adsorption, distribution, metabolism, and excretion of drugs, toxins and chemicals, and the biological process may affect the behavior of endogenous or exogenous chemicals in cells. The biological process may also be related to dermatology, pharmacology, toxicology, pathology, oncology, gastroenterology, urology, or gynecology.

In one embodiment, the first and second biological samples may originate from skin, skin appendages, oral tissue, gastrointestinal tissue, neural tissue, renal tissue, hepatic tissue, and/or urogenital tissue.

In one embodiment, a database may be created that includes the differentially expressed genes identified by the method above. In another embodiment, an informative array of sequences on a solid support may be created including sequences that are derived from the differentially expressed genes identified by the method above.

In another embodiment of the present invention, a method for selecting genes for an informative nucleic acid array for a biological process is provided. The method includes the steps of (1) identifying genes that are differentially expressed in the biological process; (2) establishing a ranking of the differentially expressed genes, wherein genes having a moderate level of expression are ranked over genes having a lower level of expression and genes having a higher level of expression; and (3) placing sequences derived from ranked differentially expressed genes on the informative array. The genes may be expressed in the biological process.

In one embodiment, the step of identifying may include the steps of (1) providing a first set of nucleic acid probes derived from a first biological sample; (2) providing a second set of nucleic acid probes derived from a second biological sample, wherein the second biological sample is dissimilar from the first biological sample; (3) hybridizing the first set of probes to the microarray and determining a first level of expression for hybridized genes; (4) hybridizing the second set of probes to the microarray and determining a second level of expression for hybridized genes; and (5) identifying genes that are differentially expressed by comparing the first level of expression with the second level of expression for hybridized genes.

According to another embodiment of the present invention, a method for converting a nucleic acid array into an informative array is disclosed. The method includes the steps of (1) providing a first set of heterogeneous nucleic acid probes derived from a first biological sample; (2) providing a different, second set of heterogeneous nucleic acid probes derived from a second biological sample; (3) hybridizing a nucleic acid array comprising a plurality of sequences with the first set of probes and determining a first level of expression for sequences of the array; (4) hybridizing the array with the second set of probes and determining a second level of expression for sequences of the array; (5) identifying a plurality of genes that are differentially expressed in the biological process by comparing the first level of expression with the second level of expression for hybridized sequences; and (6) selecting moderately expressed genes from the plurality of identified differentially expressed genes for inclusion on the informative array.

According to yet another embodiment of the present invention, an informative nucleic acid array for gene expression analysis is disclosed. The informative nucleic acid array includes sequences derived from genes of cells that are substantially relevant to a biological process; sequences derived from a plurality of differentially expressed genes that are relevant to the biological process as identified by the method for identifying genes that are differentially expressed between dissimilar biological samples for use in an informative array discussed above; and a platform for the sequences which is selected from the group consisting of a filter surface, a glass surface, a plastic surface, a solid bead surface, and a gene chip surface.

It is a technical advantage of the present invention for informative arrays to contain immobilized gene sequences that have been carefully selected from a larger set of candidate genes. It is another technical advantage of the present invention for informative arrays to increase the likelihood that the gene sequences immobilized on it will be more informative (e.g., differentially expressed) in a desired application, relative to a general array lacking a similar level of informative potential. It is another technical advantage of the present invention for informative arrays to increase the likelihood of identifying biomarkers, consisting of differentially expressed genes. Furthermore, it is another technical advantage of the present invention for informative arrays to permit reduction in the total number of gene sequences immobilized on the informative array. A reduction in the number of gene sequences may result in a reduction in the size of the informative array, due to the exclusion of non-informative genes from the list of candidate genes during the gene selection process.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE INVENTION

Figure 1:
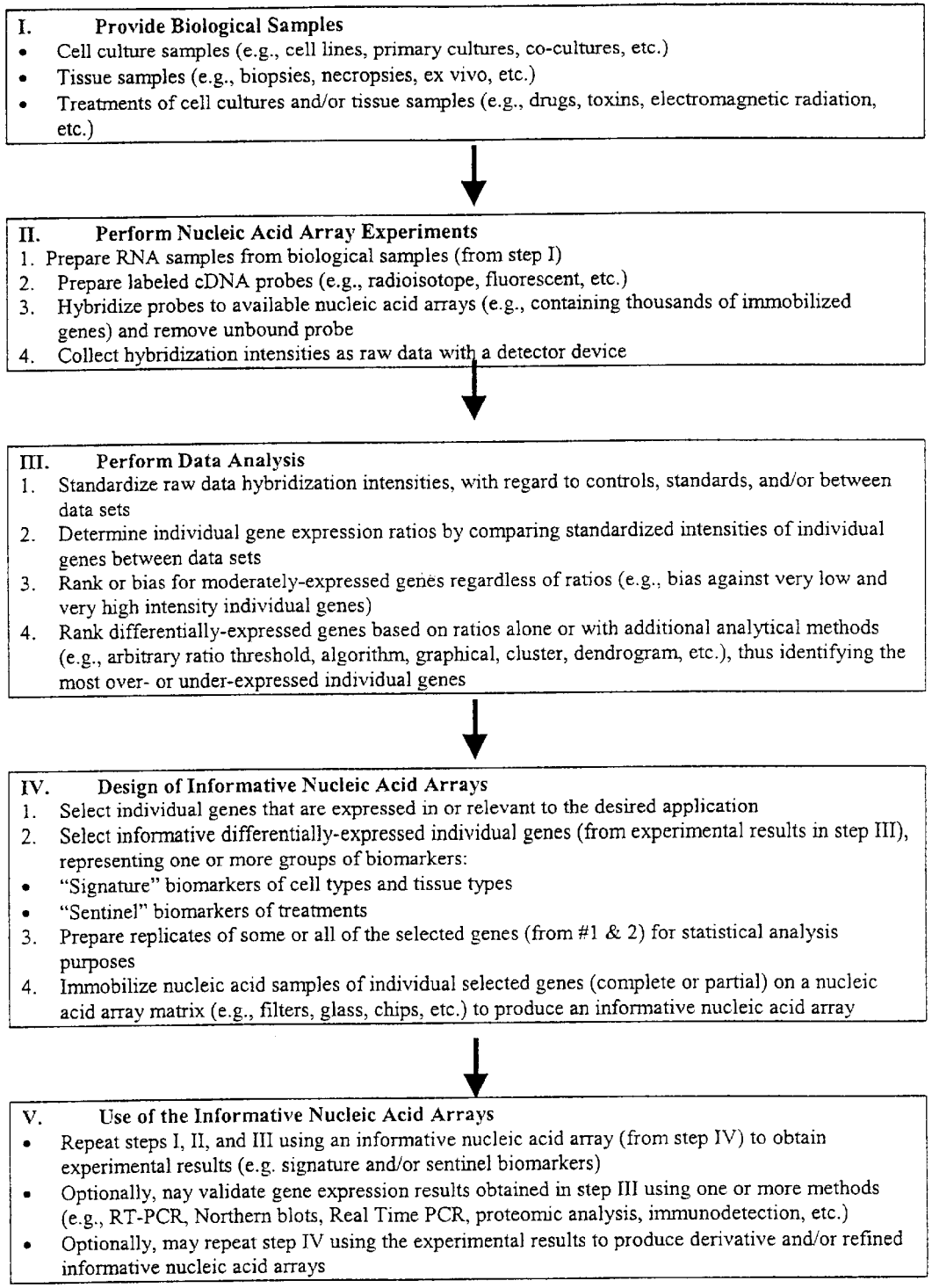
FIG. 1 depicts a flowchart representing a possible method for producing an informative nucleic acid array according to one embodiment of the present invention.
Figure 2:
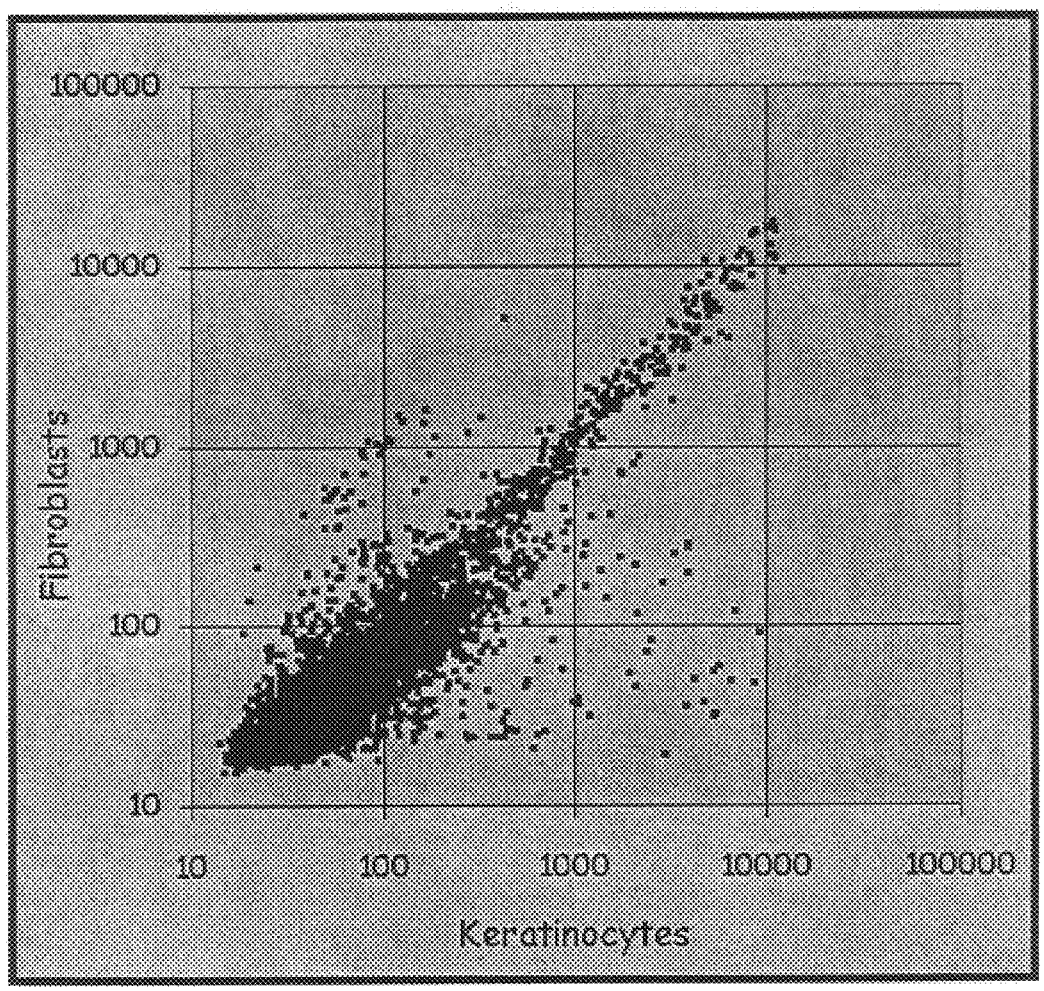
FIG. 2 depicts a plot of an experimental result using an informative array according to one embodiment of the present invention.
Figure 3:
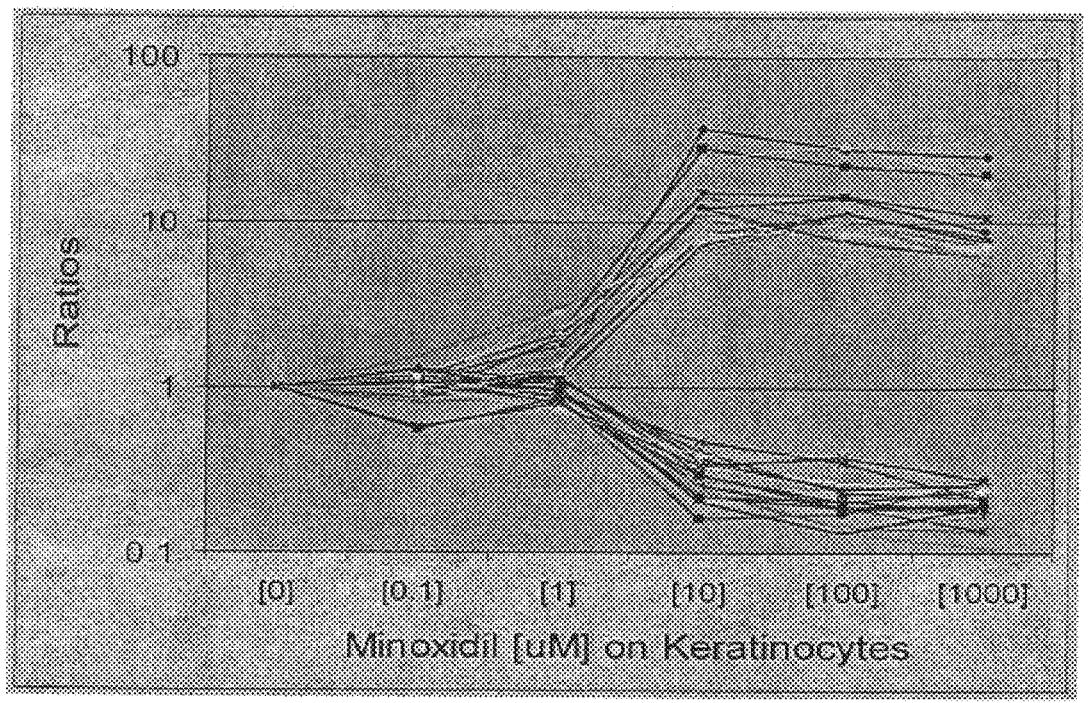
FIG. 3 depicts another plot of an experimental result using an informative nucleic acid array according to one embodiment of the present invention.

The preferred embodiment of the present invention and its advantages are best understood by referring to FIGS. 1–3 of the drawings.

It should be noted that, although the present invention is described with regard to human or mammalian genes, it is not so limited. The present invention contemplates applications with a wide variety of unicellular and multi-cellular organisms, including animals, plants, protists, fungi, etc., both living and dead (e.g., cryogenically-preserved materials from formerly living materials).

Referring to FIG. 1, a flowchart depicting a method for producing informative nucleic acid arrays ("smart arrays") according to one embodiment of the present invention is provided. The array may include isolated or purified immobilized nucleic acids, either native or synthetically created sequences, such as, for example, oligonucleotides, fragments, partial and full-length cDNAs, expressed sequence tags (ESTs), including both partial and full-length ESTs. As used herein, the phrase "nucleic acid" means any series of nucleotide sequences connected via a chemical backbone such as polydeoxyribose, polyribose, or polyamide, and is preferably DNA, RNA, or PNA. The figure schematically outlines a possible pathway for the creation and use of an informative gene list and nucleic acid array, involving 5 general steps, identified as I–V. Step I involves preparation of the biological materials. Step II involves the use of a nucleic acid gene expression array to identify differentially expressed genes. Step III involves analysis of the data sets generated from the nucleic acid array experiments. Step IV involves selection of the most informative and relevant genes for the desired application, and the subsequent creation of the informative nucleic acid array. And, Step V involves use of the informative nucleic acid array to identify biomarkers. FIG. 1 serves as an example, and is not intended to be restrictive in scope, and the invention is not so limited.

The terms "genes" and "gene sequences," as used throughout this document, includes full-length sequences of genes as well as partial gene sequences and fragments of gene sequences. A gene is any sequence of nucleotides that either detects or encodes expression of a protein or a protein fragment.

In Step I, biological samples are provided. Examples of preferred biological samples include samples of skin, skin appendages, oral tissue, gastrointestinal tissue, neural tissue, renal tissue, hepatic tissue, urogenital tissue, cells, cell cultures, cell lines, tissues, organs, organelles, biological fluids, and/or whole organisms.

In one embodiment, the biological samples may be different, or dissimilar, samples. In another embodiment, the biological samples may have a common biological process, such as adsorption, distribution, metabolism, and excretion of drugs, toxins and chemicals. The biological process may affect the behavior of endogenous or exogenous chemicals in cells.

In another embodiment, the biological process may be substantially related to dermatology, pharmacology, toxicology, pathology, oncology, gastroenterology, urology, or gynecology. Although these studies are identified, the present invention is not so limited.

In yet another embodiment, three or more biological samples are preferred.

In Steps II & III, expressed gene sequences may be identified. In one embodiment, this may include screening at least one nucleic acid array using at least one probe to identify expressed gene sequences. In one embodiment, chemically-labeled or radiolabeled (or tagged) probes that may be derived from RNA samples of biological samples may be used to identify expressed gene sequences or cross-hybridizing members of a gene family.

In Step II, a set of heterogeneous nucleic acid probes are derived from each biological sample provided in Step I. Next, a nucleic acid array is hybridized with each set of probes, and a level of expression for sequences of the array is determined and recorded. This may be accomplished with any number of commercially available detector device, such as, for example, a phosphor imager, autoradiographic film, or a fluorescence microscope, all of which are commercially available.

In one embodiment, it is preferred to perform three or more experiments.

In Step III, data analysis may be employed to identify informative differentially expressed genes. In one embodiment, differences between the measured levels of expression for each set of probes is determined. This may be achieved through any suitable method, including determining a hybridization intensity difference between the first level of expression and the second level of expression, establishing a ratio between the first level of expression and the second level of expression, establishing a ratio threshold for the first level of expression and the second level of expression, or determining a percent standard deviation for the first level of expression and the second level of expression. It is also possible to use an algorithm to quantify differences between the levels of expression, to perform cluster analysis on the levels of expression, or to perform dendrogram analysis on the levels of expression.

As discussed above, it may be advantageous and/or preferred to include a minimum of three or more dissimilar biological samples. In this example, an investigator attempts to identify examples of gene sequences wherein an individual gene is substantially over- or under-expressed in one sample but not in another. By comparing three or more samples, one may more readily characterize the specificity, selectivity, and limitation of the particular differential expression response in a plurality of biological samples or experimental contexts. Conversely, these analysis methods may also be used to detect individual gene sequences whose expression patterns are similar when comparing dissimilar probe samples, which is most often the case.

The identified differentially expressed genes may be ranked. In general, the ranking may be determined by comparing the standardized (or normalized) intensities of an individual gene compared between two or more dissimilar biological samples. The standardized or normalized value for the expression of any particular gene is arbitrary as it is simply used for comparative purposes. Thus, the value obtained from any first set of probes can be used as the standard to which subsequent sets are compared.

In one embodiment, it may be preferable to establish a ratio between the levels of expression may be used to rank the genes. For example, the larger level of expression may be compared to the smaller level of expression, yielding a ratio of expression. It may be preferred to rank genes having a ratio further from 1.0 over genes having a ratio closer to 1.0, and more preferable to rank genes having a ratio of less than 0.8 and greater than 1.2 over other genes. For instance, an individual gene might be represented as 1.6×over-expressed in one sample relative to the other, based on the experimental results. Other multipliers, such as 1.8, 2.2, and 3.0 may be used. Arbitrary or experimentally determined ratio thresholds may be used to establish criteria for inclusion and exclusion of individual candidate gene sequences in the subsequent creation of an informative nucleic acid array. For instance, one may chose only those gene sequences that are over-expressed or under-expressed by 1.6×(e.g., either 160 percent or 62.5 percent of the reference sample), 1.8, 2.2., 3.0, etc. may be used. These numbers, however are not intended to be restrictive.

In another embodiment, the ranking may be determined based on the difference in the levels of expression. For example, in one embodiment, genes having a higher difference are ranked over genes having a lower difference. Before ranking, an absolute value of the difference may be taken such that the absolute value of the difference is used to rank the genes.

In another embodiment, a standard deviation for the levels of expression may be used to rank the genes. For example, genes having a higher standard deviation may be ranked over genes having a lower standard deviation. This is especially meaningful when comparing three or more dissimilar biological samples.

In one embodiment, it may be preferable to rank genes having a moderate level of expression over genes having a lower level of expression and genes having a higher level of expression. This may increase the likelihood of identifying genes with substantial differences in the levels of expression between dissimilar probe samples. When all of the intensities of the individual gene sequences immobilized on an array have been collected from a hybridization experiment by a detector instrument and analyzed, a broad spectrum of individual gene sequences' intensities are generated.

Surprisingly, it has been noted by the inventors of the present invention that the gene sequences on a nucleic acid array that are expressed at very high levels of intensities, seldom demonstrate differential expression between dissimilar biological samples (i.e., are typically invariant). Thus, they are unlikely to provide informative responses if included in an array. This is counter-intuitive and opposite of what one of ordinary skill in the art would expect.

It has also been surprisingly noted by the inventors of the present invention that the gene sequences that are expressed at very low levels (e.g., within 2×of the intensity of the back ground for detection) on a nucleic acid array, demonstrated the greatest potential for intensity fluctuations (e.g., percent standard deviations). In other words, the very low expression level gene sequences demonstrate considerable "noise" in the signal vs. noise analyses. This may be due to the limitations of detection at or near the background intensity of probe hybridization. Thus, these noisy gene sequences may pose a problem in the analysis and determination of significance of differentially expressed gene sequences. Therefore, ranking and/or selecting may be biased against genes with very low hybridization intensities.

In Step IV, the identified gene sequences may be selected and applied to a platform. In one embodiment, the selected gene sequences may be applied to a nucleic acid array filter surface (e.g., nylon filter). In another embodiment, the identified gene sequences may be applied to a glass surface (e.g., a glass slide). In another embodiment, the identified gene sequences may be applied to a plastic surface. In another embodiment, the identified gene sequences may be applied to a gene chip. In another embodiment, a suitable platform is the compact disc-like structure disclosed in U.S. Pat. No. 5,922,617. In another embodiment, the identified gene sequences may be applied to the surfaces of individual solid beads (e.g., resin beads or glass beads). Other platforms may be used, as desired.

In Step IV.2, gene sequences that are expressed in or are relevant to the area of interest are identified. For example, in one embodiment, genes that are expressed as differentiation biomarkers, such as, for example, in skin tissue, or skin cell types (e.g., keratinocytes, melanocytes, and fibroblasts), or other epithelia are identified. Similarly, in another embodiment, genes that are implicated in pharmacology, toxicology, drug metabolism studies, etc. may be identified. The genes expressed in or relevant to the area of interest may be selected for inclusion.

Scientific literature may be consulted in order to identify these genes. In another embodiment, electronic databases may be consulted. For example, Entrez, GenBank, SwissProt, or other databases may be consulted. In yet another embodiment, other sources may be used to identify genes (e.g., commercially available sources).

An example of commercially available nucleic acid arrays that may be created by the process discussed above include Genefilters® arrays, available from Research Genetics, Inc. of Huntsville, Ala. For example, the nucleic acid arrays available include, inter alia, randomly chosen gene sequences, previously identified named gene sequences, prostate-specific gene sequences, ovary-specific gene sequences, colon-specific gene sequences, with each collection of gene sequences available on a single nucleic acid array product. An example of another commercial source of nucleic acid arrays is Affymetrix, Inc. (Palo Alto, Calif.).

In one embodiment, multiple individual gene sequences, or multiple sets of gene sequences, may be duplicated on the nucleic acid array for statistical analysis. By including some or all of the selected gene sequences in multiples (especially consisting of a minimum or three each), it becomes feasible to perform inter- and intra-filter statistical analyses (e.g., standard deviations) of hybridization intensities. It may be preferable to include a limited subset (e.g., preferably 10% or less) of the gene sequences on the filter in multiples (e.g., triplicates) and the remainder of the gene sequences in singles, so as to maximize the total number of different gene sequences on the nucleic acid array. This feature may be advantageous for the design of the informative nucleic acid array.

In addition, multiple applications for the informative nucleic acid arrays of the present invention are provided. Nucleic acid arrays may be constructed on any appropriate immobilized material surface, such as, for example, glass, plastics, nylon filters, nitrocellulose filters, silicon/metal polymers, plastics, etc. by robotic spotting technology or any other suitable means. The arrays may contain gridded nucleic acid samples (or other natural or artificial nucleic acid or PNA samples) of partial or full-length gene sequences that are expressed in a species of organism. In one embodiment, the nucleic acid arrays may be subjected to nucleic acid hybridization probes that are appropriately labeled (e.g., radiolabelled or fluorescently-tagged) and generated from RNA that is derived from cells (e.g., keratinocytes), whole or partial tissues (e.g., skin, gastrointestinal tract, reproductive tract, etc.), whole or partial organs, and whole or partial organisms. Probe sets may represent the entire number of probes obtained from the biological sample, or may be preselected to represent a subset of that entire number.

Numerous internal controls, both positive and negative, may be included on the nucleic acid array surface. The immobilized nucleic acid samples of specific gene sequences may be generated synthetically as oligonucleotides, PCR-amplification products, plasmids, or from other sources.

The hybridization experiments may include testing immobilized human gene sequences with human-derived probes, or immobilized rodent gene sequences with rodent-derived probes, or homologous probing experiments in other species, or heterologous probing experiments (e.g., immobilized human gene sequences with non-human primate-derived probes). The experiments may routinely compare a set of related probe samples from tissues or cells exposed to different treatments, or normal vs. diseased samples.

The nucleic acid arrays may be subjected to multiple probing experiments for serial comparisons of the hybridization strengths of different sources of RNA (e.g., from two different tissues).

Once the informative nucleic acid arrays are created, gene expression experiments may be performed. In one embodiment, computer software may be used to facilitate quantitation of differences in gene expression patterns between radiolabelled experimental probe samples (cDNA from mRNA) on the nucleic acid arrays. As a result, gene expression experiments that took months may be performed significantly faster. In one embodiment, gene experiments may be performed in one day or less.

The software may perform data analysis to detect differential gene expression. In one embodiment, statistical analyses may be provided to assess confidence levels for data analysis. Multiple array types and multiple experiments may be combined into a single project for rapid, comprehensive data analysis.

In one embodiment, Pathways™-series software, available from Research Genetics, Inc. of Huntsville, Ala., may be used to perform this gene expression analysis.

In one embodiment, the informative nucleic acid arrays of the present invention may be used to perform gene expression analyses on RNAs isolated from cultured cells, tissues, organs, or organisms. In another embodiment, informative nucleic acid arrays of the present invention may be used as a diagnostic device for molecular pathology, molecular toxicology, molecular pharmacology, etc. It may be used to identify signature biomarker genes and/or signature sentinel biomarker genes. A signature biomarker gene is a gene which is indicative of a cell, cell type or biological process and is constituitively expressed such as, for example, PSA gene as indicative of prostatic epithelium. A sentinel biomarker gene is a gene which is also indicative of a cell, cell type or biological process, but is transiently expressed in response to a treatment such as, for example, the cytochrome p450 gene whose expression is effected by drug exposure.

As discussed above, nucleic acid arrays according to the invention may be subjected to multiple probing experiments for serial comparisons of the hybridization strengths of different sources of RNA (e.g., from two different tissues). The general utility of nucleic acid array technology outside of the field of dermatology has been shown. The present invention recognizes that the application of nucleic acid array technology is of specific relevance and utility in dermatologic research, as evidenced by the following general examples. These examples are offered to illustrate embodiments of the invention, and should not be viewed as limiting the scope of the invention.

EXAMPLES

In order to better understand the present invention, several examples are provided. These examples do not limit the present invention in any way, and are intended to illustrate embodiments and potential applications of the present invention.

Example 1

Drug Discovery (In Vitro and In Vivo)

Potential new active ingredients (either chemical or biological) were subjected to cultured cells or to tissues (although it would require removal of a tissue sample). The agents were compared using the informative nucleic acid array to an active standard. This approach provides empirical profiles that are useful in determining the mechanism of action of a previously known or new active ingredient. This information may provide insights into the identification of appropriate molecular targets for drug discovery.

For a more specific example, referring to FIG. 3, the hair growth stimulant, minoxidil (sold commercially as Rogaine®), was applied to cultured normal human keratinocytes, to determine which genes are differentially expressed in response. Those which are substantially up- or down-regulated may serve as sentinel biomarkers for minoxidil's action, and the same gene sequences may be used in subsequent experiments to find other compounds that produce a similar sentinel biomarker response. Furthermore, the gene sequences may serve as general indicators of proliferation and/or differentiation and/or toxicity status. Other reference drugs may be selected for similar experiments, such as retinoic acid, non-steroidal anti-inflammatories, etc.

Example 2

Safety & Toxicology Testing of Products (in vitro and in vivo)

Chemical or biological agents were subjected to cultured cells or to tissues (although it would require removal of a tissue sample). The agents were compared to an active or toxic sample. This approach provides empirical profiles that may be useful in determining the mechanism of action or toxicity of a new active ingredient. Once the reference profiles are validated, use of this nucleic acid array methodology may reduce the need for animal and/or human in vivo clinical testing.

For a more specific example, the toxic compound, hydroquinone, was applied to cultured melanocytic cells (e.g., a melanoma cell line), to determine which gene sequences are differentially expressed in response to the toxin. Those which are substantially up- or down-regulated may serve as sentinel biomarkers for hydroquinone's action, and the same gene sequences may be used in subsequent experiments to find other compounds that produce a similar sentinel biomarker response. Furthermore, the gene sequences may serve as general indicators of proliferation and/or differentiation and/or toxicity status. Other toxic compounds may be used in similar experiments.

Example 3

Comparison of Normal vs. Diseased Tissues or Cells

The gene expression profiles of normal vs. diseased tissue or cells may indicate the causes and/or consequences of a genetic and/or induced pathologic disorder. For instance, the gene expression profiles of keratinocyte or lymphocyte cells from psoriasis patients may be compared to normal cells from normal patients. A plurality of potential pathologic disorders could be examined, such as cancer, inflammation, diabetes, and other disorders. Furthermore, similar experiments may be conducted to determine the differences between dissimilar cell types within a single tissue, such as keratinocytes, melanocytes, and fibroblasts within skin, for instance, as depicted in FIG. 2.

Example 4

Effects of Environmental Exposure

The comparison of treated versus untreated biological samples or cultured cells may reveal the effects of environmental exposure to radiation or other conditions, such as pressure or shear forces. For instance, exposure of biological samples to ultraviolet, infrared (or temperature), X-rays, or other forms of radiation may reveal the consequences of exposure and potential damage.

Example 5

Signature or Sentinel Biomarker Databases

The advances in the Human Genome Project (and with other species) have opened doors of opportunity to catalog for the first time on a very large scale large numbers (e.g., thousands) of the expressed gene sequences for individual cell types, tissue types, organs, and for individual pathological disorders. The large data sets obtained using informative nucleic acid arrays may establish valuable reference databases of signature and/or sentinel biomarker gene sequences for use in various other experiments. The raw and subsequently analyzed data sets can include various features, such as individual gene hybridization intensities and/or differential expression ratios between biological samples, among other possibilities. Furthermore, the gene lists, per se, used in designing the informative nucleic acid arrays may also serve as valuable biomarker databases.

Example 6

Designing Diagnostic Devices

The information gathered in experiments using informative nucleic acid arrays may be used to select one or more gene sequences for inclusion in the development and design of medical diagnostic devices for pathological analyses. The devices may contain one or more gene sequences in a product resembling an informative nucleic acid array, or may be more limited in scope (e.g., containing perhaps <100 gene sequences instead of thousands of gene sequences). The devices may also detect protein products, that are the results of gene expression from the gene sequences identified using the informative nucleic acid arrays. The use of the informative nucleic acid arrays (or databases, above) helps in ranking, prioritizing, and selecting potential diagnostic biomarkers from a large plurality of candidate gene sequences.

Example 7

Potential Gene sequences

As an example a list of potential gene sequences for inclusion in a dermatologic nucleic acid array follows. Some or all of these gene sequences (or portions thereof) may be immobilized in nucleic acid arrays, and might be additions to nucleic acid array products, such as GeneFilters® prepared by Research Genetics, Inc. An example incorporating some or all of the gene sequences within this list is the DermArray™ nucleic acid array produced by IntegriDerm, Inc. of Huntsville, Ala., and the inventors of the present invention.

Examples of Gene sequences of Relevance for Inclusion in a Dermatologic Array

| Gene Category | Gene sequences |
|---|---|
| Keratinocyte-specific | Keratin 5 & 14 (basal); Keratin 1 & 10 (suprabasal); Keratin 6 & 16 (hyperproliferative); Hair keratins; S100 gene family (e.g. calpactin 1 light chain, psoriasin); |
| | Involucrin; Loricrin; Profillagrin; Envoplakin; Desmin; Cadherins; Transglutaminase; Integrins; Protein Kinase C eta; Retinoic acid receptors; Proline-rich repeats |
| Melanocyte-specific | alpha-Melanocyte stimulating hormone; Agouti signal protein; Melanocortin receptor; Adenylate cyclase; Microopthalmia transcription factor; Tyrosinase; Tyrosinase-related protein 2 (DOPAchrome Tautomerase); Tyrosinase-related protein 1 (DHICA Oxidase); Catalase; Phenylalanine hydroxylase |
| Fibroblast-specific and extracellular matrix-specific | Collagens; Collagenases; Laminin; Elastin; Elastase; alpha1-Antitrypsin; Fibronectin; Matrix metalloproteinases; Tissue inhibitor of metalloproteinases |
| Immunomodulatory | Interleukins; Interferons; (prostaglandin synthesis); (leukotriene synthesis) |
| Cell cycle and apoptosis | p53; p16; p21 |
| Growth factors and secondary messenger signaling | Mitogen-activated protein kinase; Tyrosine kinases; G-proteins; Epidermal growth factor; EGF receptor; β Fibroblast growth factor; FGF-5; FGF receptors; Estrogen receptor; PCNA; c-Ha-ras; c-myc; Ornithine Decarboxylase |
| Transcription factors | c-fos; c-jun; AP-1 |
| Endothelium | Angiotensin-converting enzyme; VonWillebrand Factor; Endothelin; Endothelin receptor |
| Xenobiotic metabolism: | Cytochrome P450 genes; Sulfotransferases; Glutathione sulfurtransferases; UDP Glucuronosyltransferases; Rhodanese; Polycyclic aromatic hydrocarbon receptor; Peroxisome proliferator |
| Other | Nitric Oxide Synthase; Dopamine receptors; Chaperonins (HSPs); Senescence markers; DNA repair (ERCC); Photolyase; Metallothionine; Multi-drug resistance; MRP |
| Controls | Actin; Ribosomal proteins; GAPDH; Mitochondrial proteins; "total genomic DNA" |

Example 8

Differentially Expressed Gene Plots

Referring to FIG. 2 and 3, plots of differential expressed genes are provided. In FIG. 2, an example of differentially expressed genes detected using an informative array according to one embodiment of the present invention is provided. The plot of an informative nucleic acid array identifies hundreds of genes (shown as individual dots) that are differentially expressed when comparing the standardized hybridization intensities of the radiolabeled probes from the two most abundant human skin-derived cell types in culture (i.e., keratinocytes and fibroblasts). Differentially expressed genes diverge substantially from the diagonal (i.e., 1 X-axis). In this example, the differentially expressed genes represent signature biomarker genes for normal fibroblasts (upper left) and normal keratinocytes (lower right).

FIG. 3 depicts a plot of sentinel biomarker genes of minoxidil-treated cultured normal human keratinocytes are plotted as a function of minoxidil concentration (log—log scale). Each line represents an individual gene's differential expression ratio identified in hybridization experiments using radiolabeled probes from each test concentration of minoxidil. Note that some sentinel genes are up-regulated and other sentinel biomarkers are down-regulated in a dose-dependent manner.

Other embodiments and uses of the invention will be apparent to those skilled in the art from consideration of the specification and practice of the invention disclosed herein.

All references cited herein, including all U.S. and foreign patents and patent applications, are specifically and entirely hereby incorporated herein by reference, including U.S. provisional application No. 60/176,022 and U.S. provisional application No. 60/197,991, U.S. Pat. No. 5,707,807, U.S. Pat. No. 5,968,784, U.S. Pat. No. 5,807,522, and U.S. Pat. No. 5,922,617. It is intended that the specification and examples be considered exemplary only, with the true scope and spirit of the invention indicated by the following claims.

We claim:

1. A method for identifying a plurality of genes that are differentially expressed between dissimilar biological samples for use in an informative array, comprising:

provides a first set of heterogeneous nucleic acid probes derived from a first biological sample;

providing a second set of heterogeneous nucleic acid probes derived from a second biological sample;

hybridizing a nucleic acid array comprising a plurality of sequences derived from genes of a biological process with the first set of probes and determining a first level of expression for sequences of the array;

hybridizing the array with said second set of probes and determining a second level of expression for sequences of the array;

identifying a plurality of genes that are differentially expressed in said biological process by comparing the first level of expression with said second level of expression for hybridized sequences; and establishing a ranking of the identified genes by a step selected from the group of steps consisting of:

determining an absolute value of the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation.

2. The method of claim 1, wherein the biological process is selected from the group consisting of the processes of absorption, distribution, metabolism, and excretion of drugs, toxins and chemicals.

3. The method of claim 1, wherein the first and second biological samples are selected from the group consisting of samples of skin, skin appendages, oral tissue, gastrointestinal tissue, neural tissue, renal tissue, hepatic tissue, urogenital tissue and combinations thereof.

4. The method of claim 1, wherein the first and second biological samples are selected from the group consisting of samples of cells, cell cultures, cell lines, tissues, organs, organelles, biological fluids, whole organisms and combinations thereof.

5. The method of claim 1, wherein the differentially expressed genes are derived from genes of epithelial cells or tissues.

6. The method of claim 1, wherein the differentially expressed genes are derived from genes of cells selected from the group consisting of skin, skin appendages, oral tissue, gastrointestinal tissue, neural tissue, renal tissue, hepatic tissue, urogenital tissue and combinations thereof.

7. The method of claim 1, wherein the step of identifying comprises:

quantifying the difference in the first level of expression and the second level of expression for hybridized sequences by applying an algorithm to the first level of expression and the second level of expression, performing cluster analysis on the first level of expression and the second level of expression, or performing dendrogram analysis on the first level of expression and the second level of expression.

8. The method of claim 1, further comprising the step of hybridizing the array with three or more sets of probes, each derived from a different biological sample, and determining a level of expression with regard to hybridization to sequences of the array.

9. The method of claim 1, wherein the step of establishing a ranking comprises:

determining an absolute value for the difference between the first level of expression and the second level of expression for the identified genes, and ranking genes having a higher difference over genes having a lower difference.

10. The method of claim 1, wherein the step of establishing a ranking comprises:

determining a standard deviation of the difference between the first level of expression and the second level of expression and ranking genes having a higher standard deviation over genes having a lower standard deviation.

11. The method of claim 9, wherein the step of establishing a ranking of the identified genes that are differentially expressed comprises:

ranking the identified genes with a bias against more highly or more lowly expressed genes.

12. The method of claim 10, wherein the step of establishing a ranking of the identified genes that are differentially expressed comprises: ranking the identified genes with a bias against more highly or more lowly expressed genes.

13. A method for selecting a plurality of genes for an informative nucleic acid array for a biological process, comprising:

identifying genes that are differentially expressed in a biological process;

establishing a ranking of the differentially expressed genes by a step selected from the group of steps consisting of:

determining an absolute value of the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation; and placing sequences derived from ranked differentially expressed genes on the informative array.

14. The method of claim 13, wherein the genes are expressed in the biological process.

15. The method of claim 13, wherein the step of identifying comprises:

providing a first set of nucleic acid probes derived from a first biological sample;

providing a second set of nucleic acid probes derived from a second biological sample, wherein said second biological sample is dissimilar from said first biological sample;

hybridizing the first set of probes to the array and determining the first level of expression for hybridized genes;

hybridizing the second set of probes to the array and determining the second level of expression for hybridized genes; and identifying genes that are differentially expressed by comparing the first level of expression with the second level of expression for hybridized genes.

16. The method of claim 13, wherein the step of identifying comprises:

quantifying the difference in the first level of expression and the second level of expression for hybridized genes by applying an algorithm to the first level of expression and the second level of expression, performing cluster analysis on the first level of expression and the second level of expression, or performing dendrogram analysis on the first level of expression and the second level of expression.

17. The method of claim 13, further comprising applying the selected genes to a filter surface, a glass surface, a plastic surface, a solid bead, or a gene chip surface.

18. The method of claim 13, wherein the step of establishing a ranking comprises employing at least one analytical method to rank the differentially expressed genes.

19. The method of claim 13, further comprising the step of:

using the informative nucleic acid array to perform gene expression analyses on RNA isolated from cells, cell cultures, cell lines, tissues, organs, organelles, biological fluids or whole organisms.

20. The method of claim 13, further comprising the step of:

using the array to identify at least one signature biomarker gene, wherein the signature biomarker gene is expressed in a cell-specific manner, a differentiation-specific manner, or a tissue-specific manner.

21. The method of claim 13, further comprising the step of:

using the informative nucleic acid array to identify at least one sentinel biomarker gene, wherein the sentinel biomarker gene is expressed in response to treatment by an agent which comprises a drug, a toxin, a chemical, a temperature, a pressure, or electromagnetic radiation.

22. A method for converting a nucleic acid array into an informative array comprising:

providing a first set of heterogeneous nucleic acid probes derived from a first biological sample;

providing a different, second set of heterogeneous nucleic acid probes derived from a second biological sample;

hybridizing a nucleic acid array comprising a plurality of sequences with the first set of probes and determining a first level of expression for sequences of the array;

hybridizing the array with said second set of probes and determining a second level of expression for sequences of the array;

identifying a plurality of genes that are differentially expressed in said biological process based on a difference between the first level of expression and the second level of expression for identified genes, by a step selected from the group of steps consisting of:
determining an absolute value for the difference between the first level of expression and the second level of expression, and ranking genes having a higher difference over genes having a lower difference; and determining a standard deviation of the difference between the first level of expression and the second level of expression, and ranking genes having a higher standard deviation over genes having a lower standard deviation; and selecting genes from the plurality of identified differentially expressed genes for inclusion on the informative array.

23. The method of claim 13, wherein the step of establishing a ranking comprises:

determining an absolute value for the difference between the first level of expression and the second level of expression for the identified genes, and ranking genes having a higher difference over genes having a lower difference.

24. The method of claim 13, wherein the step of establishing a ranking comprises:

determining a standard deviation of the difference between the first level of expression and the second level of expression and ranking genes having a higher standard deviation over genes having a lower standard deviation.

25. The method of claim 23, wherein the step of establishing a ranking of the identified genes that are differentially expressed comprises:

ranking the identified genes with a bias against more highly or more lowly expressed genes.

26. The method of claim 24, wherein the step of establishing a ranking of the identified genes that are differentially expressed comprises:

ranking the identified genes with a bias against more highly or more lowly expressed genes.

27. The method of claim 22, wherein the step of establishing a ranking comprises:

determining an absolute value for the difference between the first level of expression and the second level of expression for the identified genes, and ranking genes having a higher difference over genes having a lower difference.

28. The method of claim 22, wherein the step of establishing a ranking comprises:

determining a standard deviation of the difference between the first level of expression and the second level of expression and ranking genes having a higher standard deviation over genes having a lower standard deviation.

29. The method of claim 27, wherein the step of establishing a ranking of the identified genes that are differentially expressed comprises:

ranking the identified genes with a bias against more highly or more lowly expressed genes.

30. The method of claim 28, wherein the step of establishing a ranking of the identified genes that are differentially expressed comprises:

ranking the identified genes with a bias against more highly or more lowly expressed genes.

* * * * *